US009949992B2

(12) United States Patent
Lyles et al.

(10) Patent No.: US 9,949,992 B2
(45) Date of Patent: *Apr. 24, 2018

(54) BISPHOSPHONATE COMPOSITIONS AND METHODS FOR TREATING AND\OR REDUCING CARDIAC DYSFUNCTION

(71) Applicant: DUKE UNIVERSITY, Durham, NC (US)

(72) Inventors: Kenneth W. Lyles, Durham, NC (US); Cathleen S. Colon-Emeric, Durham, NC (US); Christopher M. O'Connor, Durham, NC (US); Dennis Abraham, Durham, NC (US); Kent Nilsson, Athens, GA (US); Howard Rockman, Durham, NC (US); Graham Russell, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,468

(22) PCT Filed: Nov. 14, 2012

(86) PCT No.: PCT/US2012/064958
§ 371 (c)(1),
(2) Date: May 15, 2014

(87) PCT Pub. No.: WO2013/074587
PCT Pub. Date: May 23, 2013

(65) Prior Publication Data
US 2014/0296166 A1    Oct. 2, 2014

Related U.S. Application Data

(60) Provisional application No. 61/560,328, filed on Nov. 16, 2011.

(51) Int. Cl.
*A61K 31/675* (2006.01)
*A61K 45/06* (2006.01)
*A61K 31/663* (2006.01)
*A61K 31/592* (2006.01)
*A61K 31/593* (2006.01)
*A61K 31/662* (2006.01)

(52) U.S. Cl.
CPC .......... *A61K 31/675* (2013.01); *A61K 31/592* (2013.01); *A61K 31/593* (2013.01); *A61K 31/662* (2013.01); *A61K 31/663* (2013.01); *A61K 45/06* (2013.01)

(58) Field of Classification Search
CPC .... A61K 31/675; A61K 31/663; A61K 45/06; A61K 31/592; A61K 31/593; A61K 31/662; A61K 2300/00
USPC ................. 514/23, 108, 80, 89, 94
See application file for complete search history.

(56) References Cited

U.S. PATENT DOCUMENTS

| 3,962,432 A | 6/1976 | Schmidt-Dunker |
| 4,639,338 A | 1/1987 | Stahl et al. |
| 4,687,767 A | 8/1987 | Bosies et al. |
| 4,711,880 A | 12/1987 | Stahl et al. |
| 4,857,513 A | 8/1989 | Oku et al. |
| 4,927,814 A | 5/1990 | Gall et al. |
| 4,939,130 A | 7/1990 | Jaeggi et al. |
| 4,942,157 A | 7/1990 | Gall et al. |
| 4,963,536 A | 10/1990 | Oku et al. |
| 5,057,505 A | 10/1991 | Widler et al. |
| 5,157,027 A | 10/1992 | Biller et al. |
| 5,403,829 A | 4/1995 | Lehtinen et al. |
| 5,646,134 A | 7/1997 | Yates |
| 5,733,564 A | 3/1998 | Lehtinen |
| 5,965,547 A | 10/1999 | Goodship et al. |
| 6,117,856 A | 9/2000 | Binderman et al. |
| 6,255,288 B1 | 7/2001 | Goodship et al. |
| 8,052,987 B2 | 11/2011 | Horowitz et al. |
| 2002/0187184 A1 | 12/2002 | Golomb et al. |
| 2003/0064965 A1 | 4/2003 | Richter |
| 2004/0265391 A1 | 12/2004 | Dannenberg et al. |
| 2004/0266734 A1 | 12/2004 | Dannenberg et al. |
| 2005/0026871 A1 | 2/2005 | Flashner-Barak et al. |
| 2006/0051407 A1 | 3/2006 | Richter et al. |
| 2006/0069068 A1 | 3/2006 | Kajander et al. |

(Continued)

FOREIGN PATENT DOCUMENTS

DE    19738005    3/1999
EP    0600834     6/1994
(Continued)

OTHER PUBLICATIONS

Rutsch et al. Hypophosphatemia, Hyperphosphaturia, and Bisphosphonate Treatment Are Associated With Survival Beyond Infancy in Generalized Arterial Calcification of Infancy. Circ Cardiovasc Genet 1:133-140, 2008.*

(Continued)

*Primary Examiner* — Yih-Horng Shiao
(74) *Attorney, Agent, or Firm* — Marianne Fuierer; Moore & Van Allen, PLLC

(57) ABSTRACT

The present invention provides for methods and compositions for treating, reducing and/or preventing cardiac dysfunction by administering to subject a therapeutically effective amount of a bisphosphonate, prodrug thereof, functional analog or a pharmaceutically effective salt thereof in an amount sufficient to increase activity of at least one kinase in heart tissue of the subject.

10 Claims, 3 Drawing Sheets

(56) References Cited

U.S. PATENT DOCUMENTS

| | | | |
|---|---|---|---|
| 2006/0069069 | A1 | 3/2006 | Kajander et al. |
| 2006/0166937 | A1 | 7/2006 | Prescott |
| 2006/0205692 | A1 | 9/2006 | Montes et al. |
| 2006/0275294 | A1* | 12/2006 | Omoigui .................. 424/145.1 |
| 2008/0146489 | A1 | 6/2008 | Pacetti et al. |
| 2008/0193564 | A1 | 8/2008 | Horowitz et al. |
| 2008/0233097 | A1 | 9/2008 | Montesinos |
| 2009/0098200 | A1 | 4/2009 | Krayz et al. |
| 2010/0144679 | A1 | 6/2010 | Lyles |
| 2010/0215743 | A1* | 8/2010 | Leonard ............... A61K 9/2013 424/468 |
| 2011/0112053 | A1 | 5/2011 | Li et al. |

FOREIGN PATENT DOCUMENTS

| | | |
|---|---|---|
| WO | WO89/09775 | 10/1989 |
| WO | WO92/03451 | 3/1992 |
| WO | WO9221355 | 12/1992 |
| WO | WO9421266 | 9/1994 |
| WO | WO99/38998 | 8/1999 |
| WO | WO 199938998 | 8/1999 |
| WO | WO0149295 | 7/2001 |
| WO | WO0189494 | 11/2001 |
| WO | WO0197788 | 12/2001 |
| WO | WO2003086415 | 10/2003 |
| WO | WO2004024166 | 3/2004 |
| WO | WO 2004035060 | 4/2004 |
| WO | WO2004112763 | 12/2004 |
| WO | WO2005002545 | 1/2005 |
| WO | WO2005027921 | 3/2005 |
| WO | WO06019843 | 2/2006 |
| WO | WO06019844 | 2/2006 |
| WO | WO2009082437 | 7/2009 |
| WO | WO 2010033978 | 3/2010 |
| WO | WO2010062365 | 6/2010 |
| WO | WO2011028737 | 3/2011 |
| WO | WO 2011028737 | 3/2011 |

OTHER PUBLICATIONS

Briesacher, Becky A. et al., "Consequences of Poor Compliance with Bisphosphonates", Bone, 41 (2007) pp. 882-887.
Christiansen, C. et al., "Dose Dependent Effects on Bone Resorption and Formation of Intermittently Administered Intravenous Ibandronate", Osteoporosis International, vol. 14, (2003), pp. 609-613.
Claxton, Ami J. et al., "A Systematic Review of the Association Between Dose Regimens and Medication Compliance", Clinical Therapeutics, vol. 23, No. I, (2001), pp. 1296-1310.
Cramer J.A. et al., "A Systematic Review of Persistence and Compliance with Bisphosphonates for Osteoporosis", Osteoporos Int. (2007) 18: pp. 1023-1031.
Cramer, Joyce A. et al., "The Effect of Dosing Frequency on Compliance and Persistence with Bisphosphonate Therapy in Postmenopausal Women: A Comparison of Studies in the United States, the United Kingdom, and France", Clinical Therapeutics, vol. 28, No. 10, (2006), pp. 1686-1694.
Crouch, S. "The In Vitro Effect of BM.21.0955 (Ibandronate) on Monocyte Production of Inflammatory Cytokines." Blood 88 (1996), Suppl. 1, p. 158A.
Fiore, C. et al. "Bisphosphonates and Atherosclerosis." J. Endocrinol. Invest. 32 (2009), 38-43.
Lyles, Kenneth W. et al. "Zoledronic Acid and Clinical Fractures and Mortality After Hip Fracture." New England Journal of Medicine, vol. 357, No. 18, Nov. 1, 2007, pp. 1799-1809.
Need, Allan G. et al. "Vitamin D Status: Effects on Parathyroid Hormone and 1,25-dihydroxyvitamin D in Postmenopausal Women." American Journal of Clinical Nutrition, vol. 71, No. 6, Jun. 2000, pp. 1577-1581.

Ono, K. "Regulation of Calcification by Bisphosphonates." Clinical Calcium 14 (2004), 906. (Abstract only).
Recker, Robert R. et al., "Effect of Dosing Frequency on Bisphosphonate Medication Adherence in a Large Longitudinal Cohort of Women", Mayo Clinic Proc. Jul. 2005, 80 (7): pp. 856-861.
Reid, David M. et al., "Zoledronic Acid and Risedronate in the Prevention and Treatment of Glucocorticoid-Induced Osteoporosis (HORIZON): A Multicentre, Double-Blind, Double-Dummy, randomized Controlled Trial", Lancet, vol. 373, Apr. 11, 2009, pp. 1253-1263.
Reid, Ian R. et al. "Intravenous Zoledronic Acid in Postmenopausal Women with Low Bone Mineral Density." New England Journal of Medicine, vol. 346, No. 9, Feb. 28, 2002, pp. 653-661.
Seeman, E. et al., "Non-Compliance: The Achilles' Heel of Antifracture Efficacy", Osteoporos Int. (2007) 18: pp. 711-719.
Shioi, A. "Atherosclerosis and Bisphosphonate." Clinical Calcium 13 (2003), 169. (Abstract Only).
Solomon, C.G. "Bisphosphonates and Osteoporosis." New England Journal of Medicine, Feb. 28, 2002, US, vol. 346, No. 9, p. 642.
Thiebaud, D. et al., "Three Monthly Intravenous Injections of Ibandronate in the Treatment of Postmenopausal Osteoporosis", The American Journal of Medicine, vol. 103, Oct. 1997, pp. 298-307.
Tintut, Y. et al. "Recent advances in multifactorial regulation of vascular calcification." Current Opinion in Lipidology 12 (2001), 555-560.
Tuominen, O. et al. "Suppression of Viability and Acetyl-LDL Metabolism in Raw 264 Macrophage-Like and Smooth Muscles Cells by Bisphosphonates In Vitro." Methods Find Exp. Clin. Pharmacol. 24 (2002), 487 (Abstract only).
Wu, L. et al. "Zoledronate inhibits the proliferation, adhesion, and migration of vascular smooth muscle cells." Eur. J. Pharm. 602 (2009), 124-131.
Extended European Search Report, corresponding to European Patent Application No. 12849346.7, issued by the European Patent Office dated Jul. 1, 2015.
Kotsikorou, Evangelia et al. "Bisphosphonate Inhibition of Phosphoglcerate Kinase: Quantitative Structure-Activity Relationship and Pharmacophore Modeling Investigation." J. Med. Chem. 49 (2006) 6692-6703.
Park, Jae et al. "Inhibition of adenosine kinase by phosphonate and biphosphonate derivatives." Molecular and Cellular Biochemistry 283 (2006) 11-21.
Tatsuda, Yoshiki et al. "Protein kinase C is inhibited by bisphosphonates in prostate cancer PC-3 cells." European Journal of Pharmacology 627 (2010) 348-353.
Ye, Yang et al. "Inhibition of farnesylpyrophosphate synthase prevents angiotensin II-induced hypertrophic responses in rat neonatal cardiomyocytes: Involvement of the RhoA/Rho kinase pathway." FEBRS Letters 583 (2009) 2997-3003.
Armstrong, Guy P. "Aeortic Stenosis." Merck Manual, 18th edition, Japanese edition, 2006, pp. 745-748.
Arnold, Malcolm O. "Heart Failure." Merck Manual, 18th edition, Japanese edition, 2006, pp. 686-697.
de Souza, P.M. et al. "Mammalian Sterile20-like kinase 1 and the regulation of apoptosis." Biochemical Society Transactions (2004) 32:485-488.
Song, Jae J. et al. "Differential cleavage of Mst1 by caspase-7/-3 is responsible for TRAIL-induced activation of the MAPK superfamily." Cellular Signaling (2008) 20:892-906.
Japanese Office Action, corresponding to Japanese Patent Application No. 2014-542390, dated Mar. 25, 2016.
Office Action, corresponding to Chinese Patent Application No. 201280063024.0, issued by the Chinese Intellectual Property Office dated Sep. 5, 2017.

\* cited by examiner

BISPHOSPHONATE COMPOSITIONS AND METHODS FOR TREATING AND\OR REDUCING CARDIAC DYSFUNCTION

CROSS-REFERENCE TO RELATED APPLICATION

The present PCT International Application and invention claims priority to U.S. Provisional Application No. 61/560,328 filed on Nov. 16, 2011, the contents of which are incorporated by reference herein for all purposes.

BACKGROUND OF THE INVENTION

Field of the Invention

The present invention relates to reducing or inhibiting cardiac dysfunction due to heart failure by administering at least one bisphosphonate compound, and more specifically, wherein the bisphosphonate compound increases expression and/or phosphorylation of at least one kinase having biological activity in heart tissue.

Related Art in the Field

The prevalence of heart failure ("HF") has grown to epidemic proportions as the population ages. HF may be caused by many forms of heart disease. Common causes of heart failure include: narrowing of the arteries supplying blood to the heart muscle (coronary heart disease); prior heart attack (myocardial infarction) resulting in scar tissue large enough to interfere with normal function of the heart; high blood pressure; heart valve disease due to past rheumatic fever or an abnormality present at birth; primary disease of the heart muscle itself (cardiomyopathy); and infection of the heart valves and/or muscle itself (endocarditis and/or myocarditis). Each of these disease processes can lead to heart failure by reducing the strength of the heart muscle contraction, by limiting the ability of the heart's pumping chambers to fill with blood due to mechanical problems or impaired diastolic relaxation, or by filling the heart's chambers with too much blood.

Cardiovascular disease is the leading cause of death in the Western world, resulting in an estimated annual death toll of more than ten million people. Such diseases, such as chronic hypertension (high blood pressure), left ventricular hypertrophy (enlargement of the heart), and myocardial ischemia (cardiac cell injury) can culminate in heart failure.

One consequence of hypertension is generally hypertrophy. Cardiac hypertrophy is an increase in the size of the heart. In humans, hypertrophy, is the compensatory response of the myocardium (cardiac muscle) to increased work as a result of an increase in blood pressure or blood volume (hemodynamic overload). Hypertrophy of the myocardium may become increasingly harmful due to the increased metabolic requirements of the enlarged heart. Moreover, ischemic heart disease and cardiac arrhythmias may develop, increasing the risk of death. Cardiac arrhythmias may arise from abnormalities in impulse formation, impulse conduction, or a combination of both. The regulation of impulse formation and conduction involves a complex interaction between the autonomic nervous system, cardiac ion channels, and cardiac gap junctions.

Gap junctions are specialized regions of the cell membrane that directly connect the cytoplasmic compartment of two neighboring cells. In cardiomyocytes, gap junctions cluster at the intercalated disc, a unique microdomain located at the ends of adjoining cardiomyocytes that help coordinate the ordered depolarization of adjacent cardiomyocytes. The gap junction channels are composed of two hemichannels (connexons) provided by each of two neighboring cells. Each connexon consists of six proteins called connexins. The distribution of the different types of connexins (Cx) varies throughout the heart. The gap junction channel can switch between an open and a closed state by a twisting motion. The conduction of the electrical impulse takes place through the gap junctions and normally functioning gap junctions are therefore a prerequisite for normal conduction and thereby normal rhythm of the heart. Disruption of gap junction organization is a common, and highly arrhythmogenic feature, of both acquired and inherited myopathies. Moreover, dynamic remodeling of gap junctions occurs during ischemia, promoting potentially fatal arrhythmias.

Heretofore, the development of antiarrhythmic drugs has focused primarily on either the autonomic nervous system or ion channels, with little attention to pharmaceuticals that may alter gap junction stability. Further, the currently available drugs are not without negative side effects. Specifically, the negative effects fall into two general categories: the usual kinds of side effects seen with many drugs (such as allergies, insomnia, gastrointestinal disturbances, etc.), and proarrhythmia. It is proarrhythmia that poses the major problem with antiarrhythmic drugs because ion channel modulators often suppress one arrhythmia while promoting another. Proarrhythmia simply means causing cardiac arrhythmias, and as such, instead of eliminating arrhythmias these drugs can actually produce them.

Therefore, there is an immediate need for therapeutic agents that prevent and/or reverse the damage caused by myocardial dysfunction without harming healthy cells. Due to the serious side effects that limit the use of the present drugs a new class of drugs with a completely different mode of action is desirable.

SUMMARY OF THE INVENTION

The present invention includes methods and compositions for treating cardiac dysfunctions and diseases related thereto, wherein the compositions comprise at least one bisphosphonate compound or prodrug thereof in an amount to effectively increase expression of at least one kinase in heart tissue and/or increase phosphorylation of kinases in heart tissue. Such increased expression and/or phosphorylation of kinases may exhibit at least one of the following advantages including: maintaining an orderly assembly of the cardiac intercalated disc, reducing dephosphorylation of connexin 43, reducing heterogeneous expression of connexin 43, maintaining both electrical and chemical communication between cardiomyocytes through communicating gap junctions, and/or reducing gap junction permeability.

In one aspect, the invention includes a method for treating hypertrophy, heart failure, ischemic heart disease, atrial fibrillation, ischemia reperfusion injury, progressive contractile dysfunction and cardiac arrhythmias, the method comprising administering to a mammal a therapeutically effective amount of a bisphosphonate, a prodrug thereof, a functional analogue thereof or a pharmaceutically effective salt thereof in a therapeutically amount to increase expression and/or phosphorylation of heart tissue kinases thereby reducing cardiac arrhythmias and/or alterations in the cardiac intercalated disc structure.

Another aspect of the present invention relates to pharmaceutical compositions comprising a bisphosphonate or a prodrug thereof and a pharmaceutically acceptable carrier or diluent. The bisphosphonate compound may include but is not limited to zoledronic acid, risedronate, alendronate, cimadronate, clodronate, tiludronate, minodronate, bisphosphonate compounds described in WO10/33981, WO10/33980 and WO10/33978, etidronate, ibandronate, piridronate, pamidronate and functional analogues thereof.

In a still further aspect, the present invention provides for methods and agents of treatment, wherein the methods and agents of treatment comprise a therapeutically effective amount of at least one bisphosphonate, a prodrug thereof, a functional analogue thereof or a pharmaceutically effective salt thereof, wherein the therapeutically effective amount is sufficient to activate and/or increase the phosphorylation of kinases in heart tissue. The kinases may comprise one or more selected from the group consisting of extracellular signal-regulated protein kinase (ERK1/2), IκB kinase (IKK), Phosphatidylinositol 3-kinases (PI 3-kinase), protein kinase B (Akt), Jun $NH_2$-termina kinases (JNK), casein kinase-1, and p38 mitogen activated protein kinase (MAPK).

A further aspect of the present invention relates to administration of the bisphosphonate compound at least daily, weekly, monthly or annually, either as a preventive dosage or after the diagnosis of heart failure. The amount of the bisphosphonate compound administered is an amount effective to treat or prevent a patient's heart failure. The amount will depend on the mode of administration, frequency of administering the compound and can range from about 0.01 ug/kg to about 100 mg/kg. For example, a daily oral dosage can range from about 10 ug/kg to about 200 ug/kg while a yearly intravenous dose may be from about 0.002 to about 20.0 mg/kg.

Effective treatment can be exhibited by an increase of ejection fraction, increase in diastolic and/or systolic function, improvement in hemodynamics, reductions in arrhythmias, and improvement in heart rate variability, all of which can be tested by skilled artisans with known and available testing regimes.

A still further aspect of the present invention relates to the use of a bisphosphonate compound alone or together with other cardiac therapeutic agents including, but not limited to, nitrates, beta-adrenergic blockers, calcium channel antagonists, antihypertensive agents, cholesterol lowering agents, diuretics, ACE inhibitors, non-peptide angiotensin II antagonists, IIb/IIIa antagonists and aspirin in the manufacture of a medicament for the prevention of cardiovascular events, for example stroke, heart failure, cardiovascular death, myocardial infarction, worsening of angina, cardiac arrest, or need for revascularization procedures.

Another aspect of the present invention relates to a method of treating cardiovascular diseases and diseases related thereto, wherein a subject is administered Vitamin D (cholecalciferol or ergocalciferol) in dosages ranging from about 50,000-125,000 IU in a single or multiple dosages. The Vitamin D may be administered prior to, subsequent to or simultaneously with the bisphosphonate compounds.

A final aspect of the present invention relates to a kit for treatment or prevention of heart failure and negative side-effects thereof, the kit comprising at least one dose of a bisphosphonate or prodrug thereof in a therapeutically effective amount to treat, reduce or prevent the symptoms of heart failure. The kit may optionally include a sufficient daily dosage of Vitamin D for consumption before, during and after treatment with the bisphosphonate.

Other aspects, objects, features and advantages of the present invention would be apparent to one of ordinary skill in the art from the following detailed description illustrating the preferred embodiments of the invention.

DETAILED DESCRIPTION OF THE INVENTION

Figure 1:
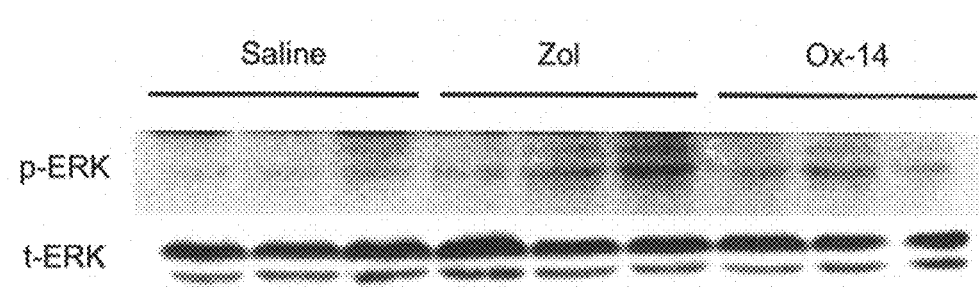
FIG. 1 is an immunoblot showing the results relating to expression of ERK and subsequent phosphorylation in myocardial lysate after bisphosphonate administration and SHAM procedures in the testing animals.

The present invention is directed to compositions and methods for treatment of heart failure including conditions such as cardiac arrhythmias, decreased cardiac contractility, abnormal diastolic or systolic compliance, reduced stroke volume and decreased cardiac output, while minimizing or attenuating deleterious effects commonly associated with previously used compounds.

Bisphosphonates, a class of compounds that are pyrophosphate analogues, have been used for thirty (30) years to treat skeletal disorders caused by increased osteoclastic bone resorption (Rosen, 2005). The first compound approved for use in treating Paget's disease of bone was etidronate. This was followed by more potent nitrogen-containing bisphosphonates, such as alendronate, risedronate and ibandronate, all of which have become the first line of therapy for postmenopausal osteoporosis. These agents can be delivered by multiple modes including orally and intravenously.

Bisphosphonates are the current drugs of choice for osteoporosis because they reduce fracture rates as well as the attendant disability (Rosen, 2005). Although two types of osteoporotic fractures (vertebral and hip) are associated with increased mortality, until recently no clinical trial using bisphosphonates to treat this disease has shown a reduction in mortality. Recently, a clinical study was conducted wherein patients who were within 90 days of surgical repair of a hip fracture were randomized to receive either zoledronic acid or placebo at baseline and yearly thereafter, with the primary response variable being the rate of new clinical fractures (Colon-Emeric et al. 2004). The trial had a positive outcome with a 35% reduction in the risk of all clinical fractures (Lyles et al. 2007). Further, a 28% reduction in mortality was observed in those patients who received zoledronic acid compared to the placebo subjects.

Another study of interest described the use of genetically engineered mice exhibiting the effects of having Hutchinson-Gilford Progeria Syndrome (HGPS). The people diagnosed with this disease usually have small, fragile bodies, like those of elderly people. Later, the condition causes wrinkled skin, atherosclerosis and cardiovascular problems. The mice were treated with pravastatin and zoledronic acid in an attempt to slow premature aging, growth retardation, vascular disease, hair loss, and osteoporosis. (Varela 2008). In combination, these therapies were reported to increase the median lifespan from 101 to 179 days.

Upon seeing the results of these studies, it was theorized by the present inventors that bisphosphonates could be responsible for the reduction in mortality and that the link between reduced mortality and bisphosphonates is likely related to activity of heart tissue kinases including increased expression and/or phosphorylation thereof. Such increased expression and/or phosphorylation of kinases, such as mitogen-activated protein kinases (MAPK), induces numerous activities that are beneficial to heart tissue including maintaining an orderly assembly of the cardiac intercalated disc, reducing dephosphorylation of connexin 43, reducing heterogeneous expression of connexin 43, maintaining both electrical and chemical communication between cardiomyocytes through communicating gap junctions, and/or reduced gap junction permeability.

This flux of materials between cells via gap junction channels is known as gap junctional intercellular communication (GJIC), which plays an important role in the regulation of cell metabolism, proliferation, and cell-to-cell signaling. The mode of GJIC regulation or junctional gating has been widely studied for gap junctions especially gap junctions composed of connexin 43, the principle gap junction located in the ventricle. Specifically, changes in the phosphorylation of specific sites of the cytoplasmic carboxy terminal domain of connexin 43 appear to be pivotal to the opening and closing of the gap junctional channel. The carboxy terminal domain of connexin 43 contains putative phosphorylation sites for multiple protein kinases including cAMP-Dependent protein kinase A (PKA), protein kinase-C (PKC), cGMP-Dependent protein kinase (PKG), mitogen-activated protein kinase (MAPK) and tyrosine kinase wherein such phosphorylation by kinases is directly or indirectly involved in the regulation of gap junctions, that being, the acute controlled gating of the gap junction channels. Importantly, it has been found that remodeling of connexin 43 gap junction distribution and overall reductions in connexin 43 levels are common features of ischemic, hypertrophic and other cardiomyopathic diseases of the heart in humans.

It is theorized that the present invention provides for a treatment that includes a group of bisphosphonate compounds that addresses such issues relating to communication between cardiac myocytes and thereby maintaining an orderly assembly of the cardiac intercalated disc.

Definitions

The term "bisphosphonate," as used herein, means any compound which is an analog of endogenous pyrophosphate whereby the central oxygen is replaced by carbon. The term "bisphosphonate" includes prodrugs thereof and aminobisphosphonates. Bisphosphonates include, but are not limited to the following compounds: zoledronic acid, risedronate, alendronate, cimadronate, clodronate, tiludronate, minodronate, bisphosphonate compounds described in WO10/33981, WO10/33980 and WO10/33978, etidronate, olpadronate, neridronate, ibandronate, piridronate, or pamidronate, functional analogues thereof and prodrugs thereof.

The term "zoledronic acid," as used herein, means to include the free acid itself, i.e., 1-hydroxy-2-(imidazol-1-yl)ethane-1,1-diphosphonic acid, as well as any pharmaceutically acceptable salts and hydrates thereof and solvates thereof formed from other solvents used for its crystallization. 1-hydroxy-2-(imidazol-1-yl)ethane-1,1-diphosphonic acid and its pharmacologically acceptable salts, hydrates and solvates are well-known from the literature. They can be prepared by procedures known in the art, such as described, e.g., in U.S. Pat. No. 4,939,130. See also U.S. Pat. Nos. 4,777,163 and 4,687,767. The contents of the latter three patents are hereby incorporated by reference in their entirety.

The term "heart failure," as used herein, means impaired cardiac function that renders the heart unable to maintain the normal blood output at rest or with exercise, or to maintain a normal cardiac output in the setting of normal cardiac filling pressure. A left ventricular ejection fraction of about 40% or less is indicative of heart failure (by way of comparison, an ejection fraction of about 55% to 60% percent is normal). Patients with heart failure display well-known clinical symptoms and signs, such as tachypnea, pleural effusions, fatigue at rest or with exercise, contractile dysfunction, atrial fibrillation and edema. Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

The term, "ischemic heart disease," as used herein, means any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

The term "myocardial infarction," as used herein, means a process by which ischemic disease results in a region of the myocardium being replaced by scar tissue.

The term "cardiomyocyte," as used herein, refers to any cell in the cardiac myocyte lineage that shows at least one phenotypic characteristic of a cardiac muscle cell. Such phenotypic characteristics can include expression of cardiac proteins or electrophysiological characteristics. As used herein, the term "cardiomyocyte" and "myocyte" are interchangeable.

The term "cardiomyopathy" as used herein, means the deterioration of the function of the myocardium (i.e., the actual heart muscle) for any reason. People with cardiomyopathy are often at risk of arrhythmia and/or sudden cardiac death. Cardiomyopathies can generally be categorized into extrinsic cardiomyopathies and intrinsic cardiomyopathies. Extrinsic cardiomyopathies are cardiac disorders where the primary pathology is outside the myocardium itself. Most cardiomyopathies are extrinsic as the underlying myocardial injury is due to extrinsic factors such as ischemia. Examples of extrinsic cardiomyopathies include ischemic cardiomyopathy and cardiomyopathy due to systemic diseases. Ischemic cardiomyopathy is a weakness in the muscle of the heart due to inadequate oxygen delivery to the myocardium with coronary artery disease being the most common cause. Intrinsic cardiomyopathies are cardiac disorders where weakness in the muscle of the heart is not due to an identifiable external cause. Intrinsic cardiomyopathies include dilated cardiomyopathy (DCM), hypertrophic cardiomyopathy (HCM or HOCM), arrhythmogenic right ventricular cardiomyopathy (ARVC), and restrictive cardiomyopathy (RCM).

The term "myocardial injury," as used herein, means injury to the muscular tissue of the heart. It may arise from myocardial infarction, cardiac ischemia/reperfusion, cardiotoxic compounds, or other causes. Myocardial injury may be either an acute or nonacute injury in terms of clinical pathology. In any case it involves damage to cardiac tissue and typically results in a structural or compensatory response.

The term "ischemia," as used herein, means a restriction in blood supply, generally due to factors in the blood vessels, with resultant damage or dysfunction of tissue (e.g., cardiac tissue). Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The term "cardiac remodeling," as used herein, means the compensatory or pathological response following myocardial injury. Cardiac remodeling is viewed as a key determinant of the clinical outcome in heart disorders. It is characterized by a structural rearrangement of the cardiac chamber wall that involves cardiomyocyte hypertrophy, fibroblast proliferation and increased deposition of extracellular matrix (ECM) proteins.

The term "treating," as used herein, means that the administration of a bisphosphonate compound slows or inhibits the progression of heart failure during the treatment, relative to the disease progression that would occur in the absence of treatment, in a statistically significant manner. Well known indicia such as left ventricular ejection fraction, exercise performance, and other clinical tests as enumerated above, as well as survival rates and hospitalization rates, event rates or composite endpoints may be used to assess disease progression. Whether or not a treatment slows or prevents disease progression in a statistically significant manner may be determined by methods that are well known in the art.

The term "analogue" as used herein, means a molecule that structurally resembles a reference molecule but which has been modified in a targeted and controlled manner, by replacing a specific substituent of the reference molecule with an alternate substituent. Compared to the reference molecule, an analogue would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

The term "preventing," as used herein, means minimizing or partially or completely inhibiting the development of heart failure in a mammal at risk for developing congestive heart failure. Determination of whether heart failure is minimized or prevented by administration of a bisphosphonate is made by known methods.

The term "therapeutically effective amount," as used herein, means an amount of a compound or combination of compounds that ameliorates, attenuates, or eliminates one or more symptoms of heart failure or prevents or delays the onset of one or more symptoms of heart failure as defined herein.

The term "pharmaceutically acceptable," as used herein, means that the carrier, diluent, excipients, and/or salt must be compatible with the other ingredients of the formulation, and not deleterious to the patient. Examples of pharmaceutically acceptable salts of the compounds include salts derived from an appropriate base, such as an alkali metal (for example, sodium, potassium), an alkaline earth metal (for example, calcium, magnesium), ammonium and $NR'^{+}_4$ (wherein R' is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4^+$, or $NR'^+_4$ (wherein R' is for example a $C_{1-4}$ alkyl group).

The term "Vitamin D," as used herein, means any from of Vitamin D and functionally active analogue including Vitamin D2 (ergocalciferol or calciferol) and Vitamin D3 (cholecalciferol); hormones including calcidiol, dihydrotachysterol and calcitriol; Vitamin D analogues or metabolites including doxercalciferol and paricalcitol.

The term "prodrug," as used herein, means biologically inactive derivatives of bisphosphonate compounds that have chemically or metabolically cleavable groups and become the biologically active bisphosphonate compound under in vivo physiological conditions. Preferably, the prodrug is sufficiently both hydrophilic and lipophilic, chemically stable, and includes promoieties that can be easily hydrolysed at a sufficient rate after entering the target tissue.

The term "heart tissue," as used herein includes, without limitation, the myocardium of the heart (including cardiomyocytes, cardiac muscle fibers, connective tissue (endomysium), nerve fibers, capillaries, and lymphatics); the endocardium of the heart (including endothelium, connective tissue, and fat cells); the epicardium of the heart (including fibroelastic connective tissue, blood vessels, lymphatics, nerve fibers, fat tissue, and a mesothelial membrane consisting of squamous epithelial cells); and any additional connective tissue (including the pericardium), blood vessels, lymphatics, fat cells, progenitor cells (e.g., side-population progenitor cells), and nervous tissue found in the heart.

The bisphosphonate is preferably used in the form of pharmaceutical compositions that contain a therapeutically effective amount of the bisphosphonate active ingredient optionally together with or in admixture with inorganic or organic, solid or liquid, pharmaceutically acceptable carriers which are suitable for administration.

The pharmaceutical compositions may be, for example, compositions for enteral, such as oral, rectal, aerosol inhalation or nasal administration; compositions for parenteral, such as intravenous or subcutaneous administration; or compositions for transdermal administration, e.g., passive or iontophoretic. Preferably, the pharmaceutical compositions are for intravenous administration. The pharmaceutical compositions may also be for direct intracoronary injection or elution from an intravascular or intracardiac device.

The particular mode of administration and the dosage may be selected by the attending physician taking into account the particulars of the patient, especially age, weight, life style, activity level, hormonal status, e.g., post-menopausal, and bone mineral density as appropriate.

Timing and location for direct intracoronary injection or targeted intravascular or intracardiac delivery of the bisphosphonate compound may depend on the disorder being treated. In one preferred embodiment, bisphosphonate treatment during an acute myocardial infarction (AMI) would preferably include at least one acute direct injection into the coronary supplying the jeopardized myocardium at the time of interventional reperfusion. In an alternative embodiment, bisphosphonate treatment after heart transplant may include direct injection into all coronary arteries after cardiac transplantation and periodically thereafter. Such patients are frequently catheterized for biopsies and other diagnostic or therapeutic procedures; these catheterizations may provide a natural opportunity for targeted delivery of bisphosphonate therapy in these disorders. In another alternative embodiment, bisphosphonate treatment of myocarditis may be performed by intracoronary injection at the time of diagnosis and periodically thereafter. In yet another alternative embodiment, bisphosphonate therapy for cardiomyopathy and various causes of HF may be administered as either a single (one-time) or periodic treatment.

Formulations in single dose unit form contain preferably from about 1% to about 90%, and formulations not in single dose unit form contain preferably from about 0.1% to about 20%, of the bisphosphonate acid active ingredient. Pharmaceutical preparations for enteral and parenteral administration are, for example, those in dosage unit forms, such as drages, tablets or capsules and also ampoules. They are prepared in a manner known per se, for example, by means of conventional mixing, granulating, confectioning, dissolving or lyophilizing processes.

For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or drage cores. Suitable carriers are especially fillers, such as sugars, for example, lactose, saccharose, mannitol or sorbitol, cellulose preparations and/or calcium phosphates, for example, tricalcium phosphate or calcium hydrogen phosphate, and also binders, such as starch pastes, using, for example, corn, wheat, rice or potato starch, gelatin, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof, such as sodium alginate. Adjuncts are especially flow-regulating agents and lubricants, for example, silicic acid, talc, stearic acid or salts thereof, such as magnesium or calcium stearate, and/or polyethylene glycol. Drage cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Coloring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticizer, such as glycerol or sorbitol. The dry-filled capsules may contain the active ingredient in the form of a granulate, for example, in admixture with fillers, such as lactose; binders, such as starches; and/or glidants, such as talc or magnesium stearate, and, where appropriate, stabilizers. In soft capsules, the active ingredient is preferably dissolved or suspended in suitable liquids, such as fatty oils, paraffin oil or liquid polyethylene glycols, it being possible also for stabilizers to be added.

Parenteral formulations are especially injectable fluids that are effective in various manners, such as intra-arterially, intramuscularly, intraperitoneally, intranasally, intradermally, subcutaneously or preferably intravenously. Such fluids are preferably isotonic aqueous solutions or suspensions which can be prepared before use, for example, from lyophilized preparations which contain the active ingredient alone or together with a pharmaceutically acceptable carrier. The pharmaceutical preparations may be sterilized and/or contain adjuncts, for example preservatives, stabilizers, wetting agents and/or emulsifiers, solubilizers, salts for regulating the osmotic pressure and/or buffers.

Suitable formulations for transdermal application include an effective amount of the bisphosphonate active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

The method of delivering a bisphosphonate compound may be delivered in a local or targeted fashion using interventional techniques. This could be accomplished by direct coronary injection in multiple clinical contexts. In one embodiment, the bisphosphonate could be directly infused into a coronary artery of a patient undergoing an emergency intervention for reperfusion during acute myocardial infarction (AMI). In this scenario, direct intracoronary infusion of the bisphosphonate compound may have a significant effect on inflammation associated with reperfusion and healing or reperfusion injury, on infarct size, on development of sequelae such as heart failure, or on clinical outcomes. In an alternative embodiment, the bisphosphonate compound could be injected into coronary arteries (for example via the left main and right coronary arteries) after heart transplantation. It is anticipated that timing, dosage, and dosage intervals would be determined based on the disease the bisphosphonate is intended to treat or prevent, as well as the clinical context in which the bisphosphonate is administered.

Additionally, the local or targeted drug delivery methods may include coupling of the bisphosphonate compound to a carrier such as a nanoparticle, stent, microsphere, or another type of particle of appropriate size, shape, and other characteristics to effect a targeted and local delivery of the therapy. Associated devices or delivery vehicles are preferably designed for intravascular or intracardiac placement. These methods may include those in which devices or delivery vehicles are designed to promote delivery of the bisphosphonate compound over time. Such methods may include, but are not limited to, intravascular or intracardiac prostheses that are coupled to or constructed entirely out of bioabsorbable polymer. Alternatively, the bisphosphonate could be eluted from another material that may be durable or bioabsorbable.

In some applications, it may be advantageous to utilize the bisphosphonate compound in a "vectorized" form, such as by encapsulation of the active agent in a liposome or other encapsulant medium, or by fixation of the active compound, e.g., by covalent bonding, chelation, or associative coordination, on a suitable biomolecule, such as those selected from proteins, lipoproteins, glycoproteins, and polysaccharides.

In another aspect, the bisphosphonate compound may be released over time through a membrane or other barrier from a patch residing in the heart or the vasculature. Further, the bisphosphonate compound may be delivered by elution from vascular paving or hydrogel, including by way of deployment of a hydrogel-coated or other drug-eluting balloon.

Still further, the bisphosphonate compound may be combined with a device that is currently used to treat cardiovascular disorders. For example, the bisphosphonate compound could be eluted, in combination with an anti-restenosis drug or alone, from a drug-eluting stent placed in the treatment of acute myocardial infarction (AMI).

In another embodiment, the present invention relates to ensuring that the subject has an adequate level of Vitamin D before the administration of the bisphosphonate compound and specifically zoledronic acid. The level of Vitamin D can be easy determined by a simple blood test that determines the level of Calcidiol (25-hydroxyvitamin D). The unit dose of Vitamin D will be determined by the specific form, the number of day of administration, age and condition of patient, and level of determined Vitamin D deficiency. For example, cholecalciferol may in a unit tablet dose of from about 400 to 5000 IU or in intramuscular form from about 50,000 units/cc to 100,000 units/cc; egocalciferol in unit capsule dose of from about 400 to 50,000 IU; oral calcitriol in a dose from about 0.10 to about 1 mcg which can be administered at least once a day or in multiple administrations; calcidiol or doxercalciferol, both of which are vitamin D analogues may be administered in dose units of from about 300 to 2000 IU.

In yet another embodiment, the present invention relates to a formulation that includes a bisphosphonate, a form of Vitamin D and optionally calcium in an essentially homogeneous mixture, wherein a solution or solid unit dose can be administered in a single dose. The single dose can be administered daily, monthly or yearly, or at some intermediate interval depending on the bisphosphonate compound.

EXAMPLES

Example 1

Testing of different bisphosphonates to determine affinity for hydroxyapatite and FFPP enzyme inhibition.

Hydroxyapatite (HAP) Affinity

Mineral affinity for hydroxyapatite was evaluated by chromatographic profiling of different bisphosphonate compounds. Hydroxyapatite (HAP) ceramic spheres (20 mm diameter, BioRad) were packed in a 0.66×6.5 cm glass column (Omnifit®). The HAP columns were attached to a Waters 650E Advanced Protein Purification System (FPLC) (Millipore) in a running buffer of 1 mM $KPO_3$ at pH 6.8. Each compound was prepared in 1 mM $KPO_3$ buffer at pH6.8 and 400 μmoles were injected into the FPLC system. The bisphosphonate compounds were eluted in a gradient of phosphate buffer, concentration increasing from 1 mM up to 1000 mM and detected by a Waters 484 UV absorbance detector (Millipore) at their optimum wavelength. The results set forth in Table 1 show the HAP retention profiles of each compound and that some compounds have longer retention times. Clearly, zoledronic and alendronate have the longest retention time and thereby having the greatest affinity for hydroxyapatite.

FPPS Inhibition

The compounds were evaluated for in vitro inhibition of human farnesyl pyrophosphate synthase (FPPS), the major molecular target of nitrogen-containing bisphosphonate compounds. Inhibition of FPPS correlates with inhibition of bone resorption in vivo. Accordingly, FPPS inhibition is an indicator of the potency of the bisphosphonate compounds. Recombinant human FPPS was expressed and purified as described in Dunford et al., J. Med. Chem., 51: 2187-2195 (2008). For kinetic analysis, 40 ng (1 pmol) of pure FPP synthase were assayed in a final volume of 100 μl buffer containing 50 mM Tris pH 7.7, 2 mM MgCl2, 0.5 mM TCEP and 20 μg/mL BSA. The concentrations of substrates, GPP and IPP (14C-IPP, 400 KBq/μmol) were 10 μM each in the standard reaction. Reactions also contained the appropriate concentration of the appropriate bisphosphonate compound. Reactions were started with the addition of enzyme at 2 μg/mL in enzyme dilution buffer (10 mM HEPES pH 7.5, 500 mM NaCl, 5% glycerol, 2 mM TCEP, 20 μg/mL BSA) and allowed to proceed for an appropriate period of time at 37° C. The reaction mixtures were then extracted with 0.4 mL of ligroin to separate reaction products from unused substrate and, after thorough mixing, 0.2 mL of the ligroin upper phase was combined with 4 mL of general purpose scintillant. The final $IC_{50}$ value was calculated. These data, shown in Table 1, demonstrate the enzyme inhibitory activity of the bisphosphonate compounds described herein and show that zoledronate, Ox-14 and Minodronate exhibit the most effective inhibition potency ($IC_{50}$) by showing that 4.1 nM, 2.5 nM and 1.9 nM, respectively, is needed to inhibit 50% of FPPS enzyme activity.

TABLE 1

| BP | Formula | FFPPS nM $IC_{50}$ | HAP mineral binding (retention time in mins) |
| --- | --- | --- | --- |
| Alendronate | (structure) | 330 | 17.5 |
| Ibandronate | (structure) | 23 | ~11 |

TABLE 1-continued

| BP | Formula | FFPPS nM IC$_{50}$ | HAP mineral binding (retention time in mins) |
|---|---|---|---|
| Risedronate | | 5.7 | 9.97 |
| Zoledronate | | 4.1 | 12.53 |
| Minodronate | | 1.9 | 10.33 |
| 1-fluoro-2-(imidazo-[1,2-α]pyridine-3-yl)-ethyl-bisphosphonic acid (Ox-14) | | 2.5 | 6.17 |

Example 2

Measuring of the Effects of Bisphosphonates on the Expression and Activation of ERK in Myocardial Tissue Methods and Materials Bisphosphonate Compounds Zoledronic acid (Zometa®, Reclast®) bone density conservation agent IUPAC: (1-hydroxy-2-imidazol-1-yl-1-phosphoethyl)phosphonic acid MF: $C_5H_{10}N_2O_7P_2$/Entrez PCompound CID: 68740

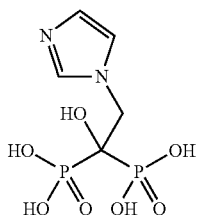

Zoledronic acid is FDA approved for the treatment of postmenopausal osteoporosis, Paget's Disease of bone, and for the prevention of skeletal complications in patients with certain cancers such as multiple myeloma and prostate cancer.

Ox-14

1-fluoro-2-(imidazo-[1,2-a]pyridine-3-yl)-ethyl-bisphosphonic acid was prepared as described in WO10/33978 and having the following structure:

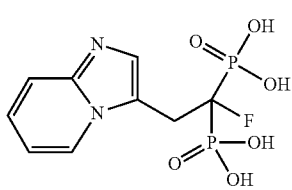 [SMILES: O=P(O)(O)C(F)(Cc1cnc2ccccn12)P(=O)(O)O]

Zoledronic Acid/Ox-14 Activity

The test dose of Zoledronic acid was 500 ug/kg and the test dose for Ox-14 was the molar equivalent of the zoledronic acid. All doses were administered subcutaneously. A 10 mM stock solution of each drug (Zoledronic acid and Ox-14) was prepared and then serially diluted 10 fold in sterile saline for a final concentration of 0.1 mM. Thus, the final stock concentration for Zoledronic acid was 0.0274 mcg/microliter and Ox-14 was 0.0391 mcg/microliter. As such, for a 25 g mouse, 12.5 mcg of Zoledronic acid was administered to achieve a dose of 500 mcg/kg. An injection 456 microliters of a 0.1 mM stock of Zoledronic acid was an appropriate dose. Likewise, injecting 456 microliters of a molar equivalent of Ox-14 delivered 17.8 mcg (712 ug/kg).

The first dose was given just prior to Transverse Aortic Constriction (TAC) on Day 0 and the second equal dose was administered on Day 3 of the protocol.

Transverse aortic constriction (TAC) was performed as previously described (Rockman, et al 1991). Briefly, adult wild type female mice were anesthetized with a 0.1 ml intraperitoneal injection of a mixture of ketamine (100 mg/kg) and xylazine (5 mg/kg). Under a dissecting microscope, (model ZDX-80; Scope Instruments, San Diego, Calif.), each animal was placed in a supine position and a midline cervical incision was made to expose the trachea. After successful endotracheal intubation, the animal was connected to a volume cycled rodent ventilator (Harvard Apparatus, Inc., South Natick, Mass.) with a tidal volume of 0.2 ml and respiratory rate of 110 breaths/min. The chest cavity was then entered in the second intercostal space at the left upper sternal border through a small incision. TAC was performed by tying a 7-0 nylon ligature against a 27-gauge needle to yield a narrowing 0.4 mm in diameter when the needle was removed. This resulted in a reproducible constriction of 65-70%. Following TAC, the pneumothorax was evacuated, and the animal was extubated and allowed to recover. Sham-operated animals underwent the same surgical procedure without TAC.

Immunodetection of myocardial kinase expression and phosphoylation was performed on myocardial lysate extract from the testing animals' hearts (with or without TAC). The myocardial kinases and any phosphorylation thereof were detected by immunoblotting for the kinases after immunoprecipitation from myocardial extracts with anti-ERK and anti-phospho-ERK antibodies. Quantification of the immunoreactivity corresponding to the total ERK and phosphorylated ERKs was carried out by densitometry.

FIG. 1 show the results using the bisphosphonates wherein all of the test animals were sham-animals, meaning the TAC ligature was not applied. Notably, whether the animal was dosed with saline, zoledronic acid or Ox 14, the level of expression of ERK did not change. However, the sham-animals that were administered the zoledronic acid showed an increase in phosphorylation of the available ERK kinase suggesting that zoledronic acid stimulated activity of the ERKs.

Figure 2:
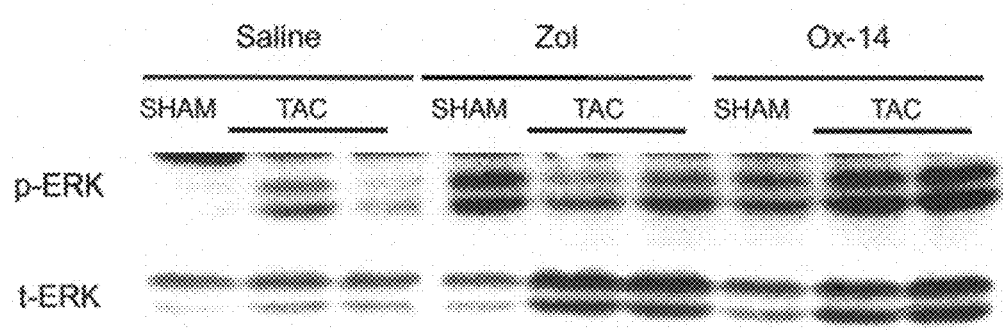
FIG. 2 is an immunoblot showing the results relating to expression of ERK and subsequent phosphorylation in myocardial lysate after administering the bisphosphonate and the SHAM or TAC procedures.

When reviewing the results as set forth in FIG. 2, it is evident that animals being administered the bisphosphonates significantly increased the levels of expression of ERK after the TAC procedures. Still further, the level of phosphorylation increased in the TAC conditioned animals with a substantial increase in the animals that were administered Ox-14. Also it is evident, as in FIG. 1, that the zoledronic acid treated SHAM group exhibited an increased level of phosphorylation that was not as evident in the Ox-14 treated SHAM group. Whether there is a signaling pathway that includes an upstream receptor or a downstream target the increase of expression and/or phosphorylation of ERK seems to be a mechanism that may play a role in the inducement of compensatory activity in heart tissue.

Figure 3:
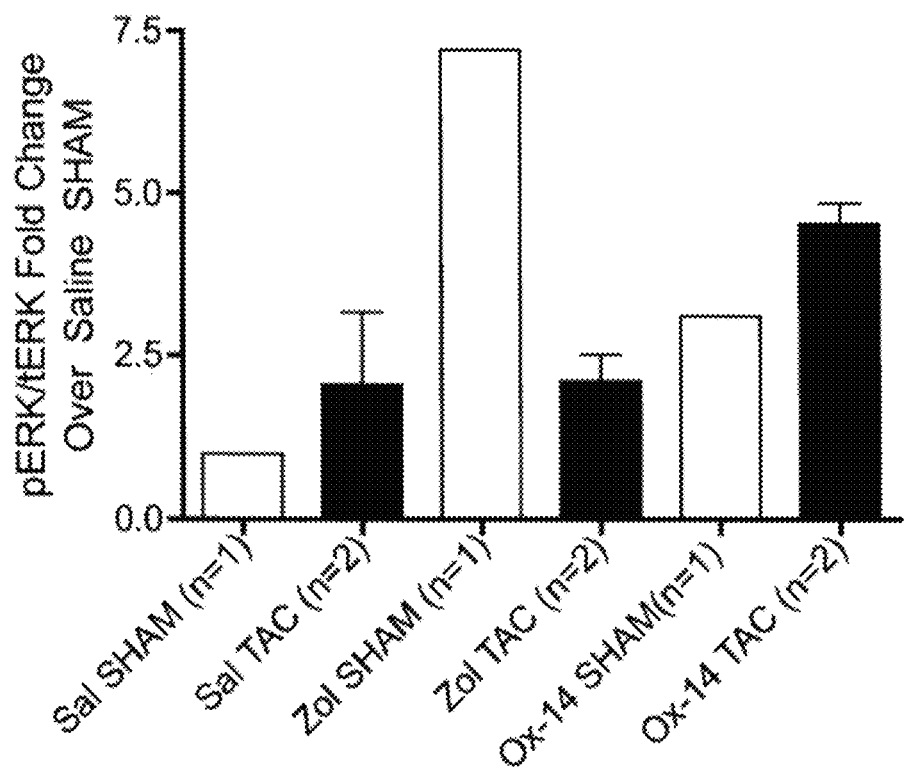
FIG. 3 is a graph showing the densitometric analysis of kinase levels from FIG. 2.

FIG. 3 shows the quantification of the pERK/tERK ratio by densitometric analysis. The values are represented as fold increases with respect to saline treated SHAM animals. Clearly there was almost a 7-fold increase of activity in the SHAM group administered zoledronic acid and about a 3-fold increase in the SHAM group administered Ox-14, both of which are due to increases in phosphorylation of the ERK as shown in FIG. 2. Interestingly there was no noticeable fold increase of activity in the zoledronic acid administered TAC group relative to the saline administered TAC group. However, there was about a 5-fold increase in the Ox-14 administered TAC group relative to the saline SHAM group and about double the activity of that of the zoledronic acid administered TAC group. The results show that bisphosphonates have the ability to act as an inducible element towards kinase activity in heart tissue.

REFERENCES

All references cited herein are hereby incorporated by reference herein for all purposes.

Colon-Emeric C, Caminis J, Suh T T, Pieper C F, Janning C, Magaziner J, Adachi J, Rosario-Jansen T, Mesenbrink P, Horowitz Z D, Lyles K W The HORIZON Recurrent Fracture Trial Design of a clinical trial in the prevention of subsequestn fractures in elders after low trauma hip fracture repair. *Curr Med Opin Res.*, 2004; 20:903-910.

Lyles K W, Colon-Emeric C S, Magaziner J S, Adachi J D, Pieper C F, Mautalen C, Hylstrup L, Recknor C, Nordsletten L, Moore K A, Lavecchia C, Zhang J, Mesenbrink P, Hodgson P K, Abrams K, Orloff J J, Horowitz Z, Eriksen E F, Boonen S. Zoledronic acid and clinical Fractures and Mortality after Hip Fracture. *N Engl J. Med.*, 2007; 357:1799-1809.

Rockman H A, Ross R, Harris A N, et al., Segregation of atrial-specific and inducible expression of an atrial natriuretic factor transgene in an in vivo murine model of cardiac hypertrophy. *PNAS*, 1991; 88: 8277-8281.

Rosen, C J. Postmenopausal Osteoporosis. *N Engl J Med.*, 2005; 353:595-603.

Varela I, Pereira S, Ugalde A P, Navarro C L, Suarez M F, Cau P, Cadinanos J, Osorio F G, Foray N, Cobo J, de Carlos F, Levy N, Freije J M P, Lopez-Otin C., Combined treatment with statins and aminobisphosphonates extends longevity in a mouse model of human premature aging. *Nature Medicine*, 2008; 14:767-772.

That which is claimed is:

1. A method for increasing activity of extracellular signal-regulated protein kinase (ERK 1/2) in heart tissue in a subject, the method comprising: orally administering to the subject an oral dosage of a bisphosphonate, wherein the bisphosphonate is administered after a diagnosis of heart failure in the subject, wherein the bisphosphonate is zoledronic acid, 1-fluoro-2-(imidazo[1,2-α]pyridine-3-yl)-ethyl-bisphosphonic acid or a pharmaceutically acceptable salt thereof in an effective dosage level from about 500 ug/kg to about 712 ug/kg, wherein the increased activity comprises (i) increased expression of ERK 1/2 kinase, (ii) increased phosphorylation of ERK 1/2 kinase in heart tissue, or (iii) a combination of both, wherein the increase in activity is relative to activity in heart tissue not being administered the bisphosphonate; and measuring the level of activity of ERK 1/2 kinase in heart tissue thereby determining the effective dosage level.

2. The method of claim 1, wherein the oral dosage is administered to the subject annually, semi-annually, monthly, weekly or daily.

3. The method of claim 1, further comprising administering to the subject at least one other therapeutic agent selected from the group consisting of nitrates, beta-adrenergic blockers, angiotensin converting enzyme (ACE) inhibitors, calcium channel antagonists, antihypertensive agents, cholesterol lowering agents, diuretics, cardiac glycosides, non-peptide angiotensin II antagonists, IIb/IIIa antagonists and aspirin.

4. The method of claim 1, wherein the heart failure results from hypertension; ischemic heart disease; exposure to a cardiotoxic compound; radiation therapy, myocarditis; thyroid disease; viral infection; drug abuse; alcohol abuse; periocarditis; atherosclerosis; vascular disease; hypertrophic cardiomyopathy; acute myocardial infarction; ventricular systolic dysfunction; ventricular diastolic dysfunction, coronary bypass surgery; or a genetic defect.

5. The method of claim 1, wherein the subject has undergone a myocardial infarction.

6. The method of claim 1, wherein the bisphosphonate is administered prior to, subsequent to or simultaneously with administering of a dosage of Vitamin D.

7. A method for increasing activity of extracellular signal-regulated protein kinase (ERK 1/2) in heart tissue in a subject, the method comprising: orally administering to the subject an oral dosage of a bisphosphonate, wherein the bisphosphonate is administered prior to a diagnosis of heart failure in the subject, wherein the bisphosphonate is zoledronic acid, 1-fluoro-2-(imidazo[1,2-α]pyridine-3-yl)-ethyl-bisphosphonic acid or a pharmaceutically acceptable salt thereof in an effective dosage level from about 500 ug/kg to about 712 ug/kg, wherein the increased activity comprises (i) increased expression of ERK 1/2 kinase, (ii) increased phosphorylation of ERK 1/2 kinase in heart tissue, or (iii) a combination of both, wherein the increase in activity is relative to activity in heart tissue not being administered the bisphosphonate; and measuring the level of activity of ERK 1/2 kinase in heart tissue to determine the effective dosage level.

8. The method of claim 7, further comprising administering to the subject at least one other therapeutic agent selected from the group consisting of nitrates, beta-adrenergic blockers, angiotensin converting enzyme (ACE) inhibitors, calcium channel antagonists, antihypertensive agents, cholesterol lowering agents, diuretics, cardiac glycosides, non-peptide angiotensin II antagonists, IIb/IIIa antagonists and aspirin.

9. The method of claim 7, wherein the heart failure results from hypertension; ischemic heart disease; exposure to a cardiotoxic compound; radiation therapy, myocarditis; thyroid disease; viral infection; drug abuse; alcohol abuse; periocarditis; atherosclerosis; vascular disease; hypertrophic cardiomyopathy; acute myocardial infarction; ventricular systolic dysfunction; ventricular diastolic dysfunction, coronary bypass surgery; or a genetic defect.

10. A method for increasing activity of extracellular signal-regulated protein kinase (ERK 1/2) in heart tissue in a subject, the method comprising: orally administering to the subject an oral dosage of a bisphosphonate, wherein the bisphosphonate is administered after a diagnosis of heart failure in the subject, wherein the bisphosphonate is zoledronic acid, 1-fluoro-2-(imidazo[1,2-α]pyridine-3-yl)-ethyl-bisphosphonic acid or a pharmaceutically acceptable salt thereof in an effective dosage level sufficient to increase activity of ERK1/2 in heart tissue of the subject, wherein the increased activity comprises (i) increased expression of ERK 1/2 kinase, (ii) increased phosphorylation of ERK 1/2 kinase in heart tissue, or (iii) a combination of both, wherein the increase in activity is relative to activity in heart tissue not being administered the bisphosphonate; and measuring the level of activity of ERK 1/2 kinase in heart tissue thereby determining the effective dosage level.

\* \* \* \* \*